United States Patent
Lion et al.

(10) Patent No.: US 10,632,058 B2
(45) Date of Patent: Apr. 28, 2020

(54) PHOSPHONIC COPOLYMER AND USE THEREOF IN THE COSMETICS FIELD

(71) Applicant: L'OREAL, Paris (FR)

(72) Inventors: Bertrand Lion, Paris (FR); Laurent Sabatie, La Varenne Saint Hilaire (FR)

(73) Assignee: L'OREAL, Paris (FR)

( * ) Notice: Subject to any disclaimer, the term of this patent is extended or adjusted under 35 U.S.C. 154(b) by 142 days.

(21) Appl. No.: 15/321,290

(22) PCT Filed: Jun. 25, 2015

(86) PCT No.: PCT/EP2015/064429
§ 371 (c)(1),
(2) Date: Apr. 17, 2017

(87) PCT Pub. No.: WO2015/197778
PCT Pub. Date: Dec. 30, 2015

(65) Prior Publication Data
US 2017/0252283 A1    Sep. 7, 2017

(30) Foreign Application Priority Data

Jun. 25, 2014 (FR) .................................. 14 55877

(51) Int. Cl.
| | | |
|---|---|---|
| *A61K 8/81* | (2006.01) | |
| *A61Q 19/08* | (2006.01) | |
| *C08F 220/18* | (2006.01) | |
| *C08L 33/10* | (2006.01) | |
| *C08L 33/08* | (2006.01) | |
| *C08F 230/02* | (2006.01) | |
| *C08L 43/02* | (2006.01) | |
| *A61K 8/58* | (2006.01) | |
| *A61K 8/898* | (2006.01) | |
| *A61K 8/90* | (2006.01) | |

(52) U.S. Cl.
CPC ............ *A61K 8/8152* (2013.01); *A61K 8/585* (2013.01); *A61K 8/898* (2013.01); *A61K 8/90* (2013.01); *A61Q 19/08* (2013.01); *C08F 220/18* (2013.01); *C08F 230/02* (2013.01); *C08L 33/08* (2013.01); *C08L 33/10* (2013.01); *C08L 43/02* (2013.01); *A61K 2800/596* (2013.01); *A61K 2800/87* (2013.01); *A61K 2800/884* (2013.01); *C08F 2220/1833* (2013.01)

(58) Field of Classification Search
CPC ............ C08F 230/02; C08F 2220/1875; C08F 220/18; C08F 2220/1833; C08L 33/08; C08L 33/10; C08L 43/02; A61K 8/898; A61K 8/585; A61K 8/81; A61K 8/90; A61K 8/8152
See application file for complete search history.

(56) References Cited

U.S. PATENT DOCUMENTS

| | | | |
|---|---|---|---|
| 6,268,454 B1 | 7/2001 | Song et al. | |
| 2006/0030686 A1* | 2/2006 | Lion ................... | A61K 8/8152 526/319 |

FOREIGN PATENT DOCUMENTS

| | | |
|---|---|---|
| EP | 1621560 A1 | 2/2006 |
| EP | 1776946 A2 | 4/2007 |
| EP | 1800659 A1 | 6/2007 |

* cited by examiner

*Primary Examiner* — Kortney L. Klinkel
(74) *Attorney, Agent, or Firm* — Polsinelli PC

(57) ABSTRACT

The invention relates to a copolymer resulting from the polymerization of:

(i) 70% to 95% by weight, of the total weight of the monomers, of isobornyl (meth)acrylate;

(ii) 1% to 30% by weight of vinylphosphonic acid monomer;

(iii) 0 to 20% by weight of an additional monomer.

The invention also relates to a cosmetic composition comprising the copolymer and to a cosmetic process for caring for or making up keratin materials, comprising the topical application of the composition to the keratin materials.

It also relates to the use of the copolymer as a skin-tensioning agent.

30 Claims, No Drawings

PHOSPHONIC COPOLYMER AND USE THEREOF IN THE COSMETICS FIELD

CROSS REFERENCE TO RELATED APPLICATIONS

This application is a National Phase filing under 35 U.S.C. § 371 of PCT/EP2015/064429 filed on Jun. 25, 2016; and this application claims priority to Application No. 1455877 filed in France on Jun. 25, 2014 under 35 U.S.C. § 119. The entire contents of each application are hereby incorporated by reference.

The present invention relates to novel polymers comprising a phosphonic acid group and to the use thereof in the cosmetics field.

During the aging process, various signs appear on the skin, which are very characteristic of this aging, resulting in particular in a modification of skin structure and functions. The main clinical signs of skin aging are in particular the appearance of fine lines and deep wrinkles, which increase with age.

It is known practice to treat these signs of aging using cosmetic or dermatological compositions containing active agents capable of combating aging, such as α-hydroxy acids, β-hydroxy acids and retinoids. These active agents act on wrinkles by eliminating dead skin cells and by accelerating the cell renewal process. However, these active agents have the drawback of only being effective for the treatment of wrinkles after a certain application time. As it happens, it is increasingly sought to obtain an immediate effect of the active agents used, rapidly resulting in smoothing-out of wrinkles and fine lines and in the disappearance of the signs of fatigue.

The inventors have discovered that novel polymers comprising a phosphonic acid group make it possible to obtain a homogeneous transparent (non-whitish) film which does not crumble, unlike similar copolymers containing acrylic acid in place of the phosphonic acid monomer. The film also has the property of not being tacky and of not transferring on contact with a finger.

Such polymers also have an improved tensioning effect on the skin and thus make it possible to immediately reduce skin wrinkles. Furthermore, when the phosphonic polymer is combined with a particular amine compound, the tensioning effect obtained is further improved and this effect exhibits, in addition, good water resistance and therefore good persistence with respect to water.

These film-forming polymers are also suitable for making up keratin materials, in particular for making up the skin or the lips, such as foundations or lipsticks.

More precisely, a subject of the present invention is a copolymer resulting from the polymerization of:
(i) 70% to 95% by weight, of the total weight of the monomers, of isobornyl (meth)acrylate;
(ii) 1% to 30% by weight of vinylphosphonic acid monomer of formula (I) defined hereinafter;
(iii) 0 to 20% by weight of an additional monomer.

Such a copolymer is referred to hereinbelow as a phosphonic polymer.

A subject of the invention is also a composition comprising, in a physiologically acceptable medium, a phosphonic polymer as described previously.

A subject of the invention is also a process, in particular a cosmetic process, for caring for or making up keratin materials, in particular the skin, comprising the topical application to the keratin materials, in particular the skin, of a composition, in particular a cosmetic composition, comprising a phosphonic polymer as described previously.

A subject of the invention is in particular a process, in particular a cosmetic process, for caring for or making up the skin or the lips, more particularly facial skin, in particular wrinkled skin, comprising the topical application to the skin of a composition, in particular a cosmetic composition, comprising a phosphonic polymer as described previously.

A subject of the invention is also a process, in particular a cosmetic process, for caring for the skin, more particularly facial skin, in particular wrinkled skin, comprising the topical application to the skin of a composition, in particular a cosmetic composition, comprising a phosphonic polymer as described previously.

The process according to the invention is in particular intended for smoothing out human facial and/or body skin and/or for decreasing or effacing the signs of skin aging, in particular for reducing or effacing wrinkles and/or fine lines on the skin.

According to one embodiment of the process according to the invention, the topical application, to keratin materials, in particular to the skin, of an extemporaneous mixture of a composition comprising a phosphonic polymer as described previously and of an amine compound, or of a composition containing same and comprising a physiologically acceptable medium, as defined hereinafter, is carried out.

According to another embodiment of the process according to the invention, the sequential application, to keratin materials, in particular to the skin, of a composition comprising a phosphonic polymer as described previously and of an amine compound, or of a composition containing same and comprising a physiologically acceptable medium, as defined hereinafter, is carried out.

A subject of the invention is also the cosmetic use, as a tensioning agent for the skin, in particular for wrinkled skin, of a phosphonic polymer as described previously, optionally as a mixture with an amine compound, or of a composition containing same and comprising a physiologically acceptable medium, as defined below.

A subject of the invention is also a composition, in particular a cosmetic composition, obtained by mixing a composition comprising said phosphonic polymer as described previously and an amine compound or a composition containing same and comprising a physiologically acceptable medium, as defined hereinafter.

A subject of the invention is also a kit comprising a first composition comprising said phosphonic polymer as described previously and a second composition comprising an amine compound as described hereinafter and comprising a physiologically acceptable medium, the first and second compositions each being packaged in a separate packaging assembly.

The composition packaging assembly is, in a known manner, any packaging that is suitable for storing cosmetic compositions (in particular a bottle, tube, spray bottle or aerosol bottle).

Such a kit allows the skin treatment process according to the invention to be performed.

The phosphonic polymer according to the invention comprises an isobornyl (meth)acrylate, a vinylphosphonic acid monomer of formula (I) and optionally an additional monomer as defined hereinafter.

The vinylphosphonic acid monomer corresponds to the following formula (I):

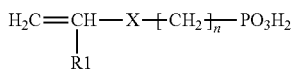 (I)

in which:
R1 denotes H or —CH$_3$;
X denotes a covalent bond and n denotes an integer ranging from 0 to 14;
or X denotes a —COO— group and n denotes an integer ranging from 2 to 6.

Advantageously, for the monomer of formula (I), X denotes a covalent bond and n is an integer ranging from 0 to 6 or X denotes a —COO— group and n is an integer ranging from 2 to 4.

Preferentially, for the monomer of formula (I):

R1=H

X denotes a covalent bond and n is an integer ranging from 0 to 4.

As examples of monomer of formula (I), the following can be cited:
vinylphosphonic acid;
3-butenylphosphonic acid;
4-pentenylphosphonic acid;
10-undecenylphosphonic acid;
11-dodecenylphosphonic acid;
2-phosphonoethyl ester of 2-propenoic acid;
2-phosphonoethyl ester of 2-methyl-2-propenoic acid.

Preferentially, the monomer (I) is vinylphosphonic acid.

The additional monomer optionally present is different than the isobornyl (meth)acrylate and vinylphosphonic acid monomers.

In particular, the additional monomer may be chosen from the monomers of formula (II):

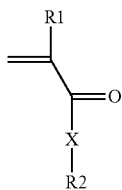 (II)

in which:
R$_1$ denotes a hydrogen atom or a methyl radical;
X denotes O or NH or NR$_3$;
R$_2$ denotes a linear C$_1$-C$_{22}$ or branched C$_3$-C$_{10}$ or cyclic C$_5$-C$_7$ alkyl radical, or a linear C$_3$-C$_{20}$ or branched C$_6$-C$_{20}$ or cyclic C$_5$-C$_7$ unsaturated hydrocarbon-based radical, or an —(Si(CH$_3$)$_2$ O)$_b$—CH$_3$ radical, with b ranging from 5 to 70, it being understood that X=O when R$_2$ is a radical of formula —(Si(CH$_3$)$_2$ O)$_b$—CH$_3$;
R$_3$ denotes a linear C$_1$-C$_{12}$ or branched C$_3$-C$_{12}$ alkyl radical.

As alkyl radical, mention may be made of the methyl, ethyl, propyl, isopropyl, butyl, tert-butyl, pentyl, isopentyl, hexyl, heptyl, octyl, isooctyl, nonyl, decyl, undecyl, lauryl, myristyl, palmityl, stearyl, eicosyl and behenyl radicals.

According to one preferred embodiment, the copolymer is free of any additional monomer.

Advantageously, copolymers of isobornyl (meth)acrylate and of vinylphosphonic acid are used.

The polymer according to the invention is preferably chosen from the copolymers resulting from the polymerization of:
70% to 95% by weight, of the total weight of the monomers, of isobornyl (meth)acrylate;
5% to 30% by weight of vinylphosphonic acid monomer of formula (I) as described previously.

Preferentially, the polymer according to the invention is chosen from the copolymers resulting from the polymerization of:
75% to 95% by weight, of the total weight of the monomers, of isobornyl (meth)acrylate;
5% to 25% by weight of vinylphosphonic acid monomer of formula (I) as described previously.

According to one preferred mode of the invention, the polymer is chosen from the copolymers resulting from the polymerization of:
70% to 95% by weight, of the total weight of the monomers, of isobornyl (meth)acrylate;
5% to 30% by weight of vinylphosphonic acid;
and preferentially of:
75% to 95% by weight, of the total weight of the monomers, of isobornyl (meth)acrylate;
5% to 25% by weight of vinylphosphonic acid.

As examples of copolymers according to the invention, mention may be made of isobornyl acrylate/vinylphosphonic acid copolymers, in particular 80/20 or 90/10 (weight/weight) isobornyl acrylate/vinylphosphonic acid copolymers.

The copolymer may be a random, alternating (block) or gradient polymer. Preferably, the copolymer is random.

The copolymer according to the invention may be prepared by radical polymerization of the monomers described previously, in particular as a mixture or added sequentially during the polymerization, in particular using an organic solvent with a boiling point of greater than or equal to 60° C., for instance isododecane, ethanol, ethyl acetate, tetrahydrofuran, methyltetrahydrofuran or methyl ethyl ketone. The organic solvent makes it possible to dissolve the monomers used and the polymer formed.

The polymerization is in particular performed in the presence of a radical initiator in particular of peroxide type (for example tert-butyl peroxy-2-ethylhexanoate: Trigonox 21S; 2,5-dimethyl-2,5-bis(2-ethylhexanoylperoxy)hexane: Trigonox 141; tert-butyl peroxypivalate: Trigonox 25C75 from AkzoNobel) or of azo type, for example (AIBN: azobisisobutyronitrile; V50: 2,2'-azobis(2-amidinopropane) dihydrochloride).

The polymerization may be performed at a temperature ranging from 60 to 100° C., and preferably ranging from 60 to 85° C.

The polymerization time may be about 24 hours.

The term "tensioning agent" is intended to mean compounds that are capable of having a noticeable tensioning effect, i.e. of smoothing out the skin and immediately reducing the wrinkles and fine lines, or even making them disappear.

The tensioning effect may be characterized by means of an in vitro retraction test as described in Example 5.

Preferably, the phosphonic polymer according to the invention has a weight-average molecular weight ranging from 5000 to 1 000 000 daltons, more preferentially ranging from 10 000 to 500 000 daltons, and even more preferentially ranging from 15 000 to 350 000 daltons. The molecular weight may in particular be determined by steric exclusion chromatography, with THF+0.2 M LiCl eluent, polystyrene standard, 2414 refractometric detector from Waters.

The phosphonic polymer as defined previously may be present in the composition according to the invention in a content ranging from 0.1% to 10% by weight, relative to the total weight of the composition, preferably from 0.5% to 10% by weight, preferentially ranging from 1% to 8% by weight, and more preferentially ranging from 1% to 6% by weight.

According to a first embodiment of the process according to the invention, an extemporaneous mixture of the phosphonic polymer according to the invention and of an additional component as defined hereinafter is prepared and the mixture is applied to the skin.

According to a second embodiment of the process according to the invention, on the one hand the phosphonic polymer and, on the other hand, an additional component as defined hereinafter are sequentially applied.

The additional component used in the process according to the invention is in particular an amine compound chosen from amine compounds containing several primary amine and/or secondary amine groups or alternatively aminosilanes. It may thus be chosen from aminosilane compounds, diamine compounds and triamine compounds or polyamine compounds.

According to a first embodiment of the invention, the amine compound is a compound comprising from 2 to 20 carbon atoms, in particular a non-polymeric compound. The term "non-polymeric compound" is intended to mean a compound which is not directly obtained via a monomer polymerization reaction.

Amine compounds that may be mentioned include N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine, lysine, cystamine, xylenediamine, tris(2-aminoethyl)amine and spermidine.

The amine compound may also be chosen from aminosilanes, such as those of formula (III):

$$R'_1Si(OR'_2)_z(R'_3)_x \quad\quad (III)$$

in which:
R'$_1$ is a linear or branched, saturated or unsaturated, cyclic or acyclic C$_1$-C$_6$ hydrocarbon-based chain substituted with a group chosen from the following groups:
amine NH$_2$ or NHR with R=C$_1$-C$_4$ alkyl,
an aryl or aryloxy group substituted with an amino group or with a C$_1$-C$_4$ aminoalkyl group,
R'$_1$ possibly being interrupted in its chain with a heteroatom (O, S, NH) or a carbonyl group (CO), R'$_1$ being linked to the silicon atom directly via a carbon atom,
R'$_2$ and R'$_3$, which may be identical or different, represent a linear or branched alkyl group comprising from 1 to 6 carbon atoms,
z denotes an integer ranging from 1 to 3, and
x denotes an integer ranging from 0 to 2,
with z+x=3.

Preferably, R'$_2$ represents an alkyl group comprising from 1 to 4 carbon atoms.

Preferably, R'$_2$ represents a linear alkyl group comprising from 1 to 4 carbon atoms.

Preferably, R'$_2$ represents an ethyl group.

Preferably, R'$_3$ represents an alkyl group comprising from 1 to 4 carbon atoms.

Preferably, R'$_3$ represents a linear alkyl group comprising from 1 to 4 carbon atoms.

Preferably, R'$_3$ represents a methyl or ethyl group.

Preferably, R'$_1$ is an acyclic chain.

Preferably, R'$_1$ is a linear or branched, saturated or unsaturated C$_1$-C$_6$ hydrocarbon-based chain, substituted with an amine group NH$_2$ or NHR (R=C$_1$-C$_6$ alkyl, C$_3$-C$_6$ cycloalkyl or C$_6$ aromatic). Preferentially, R'$_1$ is a saturated linear C$_1$-C$_6$ hydrocarbon-based chain substituted with an amine group NH$_2$. More preferentially, R'$_1$ is a saturated linear C$_2$-C$_4$ hydrocarbon-based chain substituted with an amine group NH$_2$.

Preferably, R'$_1$ is a saturated linear C$_1$-C$_6$ hydrocarbon-based chain substituted with an amine group NH$_2$,
R'$_2$ represents an alkyl group comprising from 1 to 4 carbon atoms,
R'$_3$ represents an alkyl group comprising from 1 to 4 carbon atoms.

Preferably, z is equal to 3.

Preferably, the aminosilane of formula (III) is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy) propyltrimethoxysilane, p-aminophenyltrimethoxysilane and N-(2-aminoethylaminomethyl) phenethyltrimethoxysilane.

Preferably, the aminosilane (III) is chosen from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane.

Preferably, the aminosilane (III) is 3-aminopropyltriethoxysilane (APTES).

Preferably, the amine compound is chosen from 3-aminopropyltriethoxysilane (APTES), N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl) aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine and lysine.

The amine compound may also be chosen from amine-based polymers, in particular having a weight-average molecular weight ranging from 500 to 1 000 000, preferably ranging from 500 to 500 000, and preferentially ranging from 500 to 100 000.

As amine-based polymer, use may be made of poly((C$_2$-C$_5$)alkyleneimines), and in particular polyethyleneimines and polypropyleneimines, in particular poly(ethyleneimine)s (for example the product sold under the reference 46,852-3 by the company Aldrich Chemical); poly (allylamine) (for example the product sold under the reference 47,913-6 by the company Aldrich Chemical); polyvinylamines and copolymers thereof, in particular with vinylamides; mention may in particular be made of vinylamine/vinylformamide copolymers such as those sold under the name Lupamin® 9030 by the company BASF; polyamino acids bearing NH$_2$ groups, such as polylysine, for example the product sold by the company JNC Corporation (formerly Chisso); aminodextran, such as the product sold by the company CarboMer Inc; amino polyvinyl alcohol, such as the product sold by the company CarboMer Inc, acrylamidopropylamine-based copolymers; chitosans; polydimethylsiloxanes comprising primary amine groups at the chain end or on side chains, for example aminopropyl side or end groups, for instance those of formula (A) or (B) or (C):

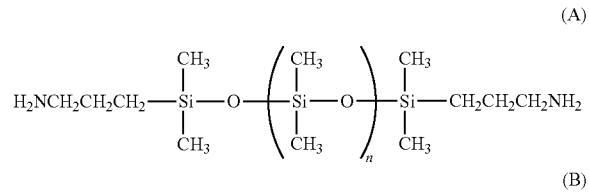

(A)

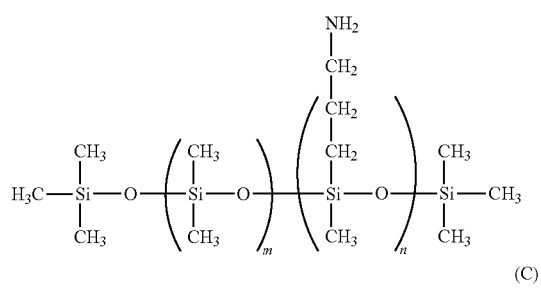

(B)

$H_2NCH_2CH_2CH_2-Si(CH_3)_2-O-[Si(CH_3)_2-O]_n-Si(CH_3)_2C_4H_9$ (C)

in formula (A): the value of n is such that the weight-average molecular weight of the silicone is between 500 and 55 000. As an example of aminosilicone (A), mention may be made of those sold under the names DMS-A11, DMS-A12, DMS-A15, DMS-A21, DMS-A31, DMS-A32 and DMS-A35 by the company Gelest;
in formula (B), the values of n and m are such that the weight-average molecular weight of the silicone is between 1000 and 55 000. As examples of silicone (B), mention may be made of those sold under the names AMS-132, AMS-152, AMS-162, AMS-163, AMS-191 and AMS-1203 by the company Gelest;
in formula (C), the value of n is such that the weight-average molecular weight of the silicone is between 500 and 3000. As an example of silicone (C), mention may be made of those sold under the names MCR-A11 and MCR-A12 by the company Gelest;
amodimethicones of formula (D):

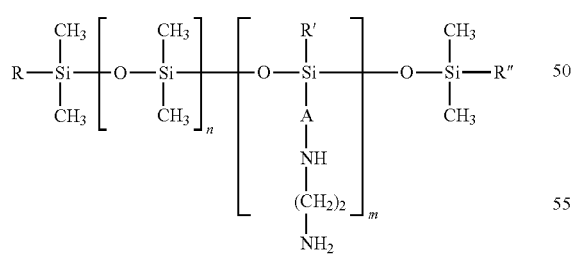

(D)

in which R, R' and R", which may be identical or different, each represent a $C_1$-$C_4$ alkyl or hydroxyl group, A represents a $C_3$ alkylene group and m and n are such that the weight-average molecular mass of the compound is between 5000 and 500 000 approximately;
the polyether amines known in particular under the reference Jeffamine from the company Huntsman; and in particular: polyethylene glycol and/or polypropylene glycol α,ω-di-amines (bearing a chain-end amine function), such as those sold under the names Jeffamine D-230, D-400, D-2000, D-4000, ED-600, ED-9000, ED-2003;
polytetrahydrofuran (or polytetramethylene glycol) α,ω-diamines;
polybutadiene α,ω-diamines;
polyamidoamine (PANAM) dendrimers bearing amine end functions;
poly(meth)acrylates or poly(meth)acrylamides bearing primary or secondary amine side functions, such as poly(3-aminopropyl)methacrylamide or poly(2-aminoethyl) methacrylate.

As amine-based polymer, use is preferably made of polyethylene glycol and/or polypropylene glycol α,ω-di-amines and polydimethylsiloxanes comprising aminopropyl end groups.

Preferentially, the amine compounds used in the process according to the invention are chosen from ethylenediamine, lysine and 3-aminopropyltriethoxysilane (APTES). More preferentially, 3-aminopropyltriethoxysilane (APTES) is used.

Advantageously, the amine compound used in the process according to the invention is used according to an amine compound/phosphonic acid mole ratio ranging from 0.01 to 10, preferably ranging from 0.1 to 5, preferentially ranging from 0.1 to 2 and more preferentially ranging from 0.1 to 1.

On contact with the phosphonic polymer, the amine compound reacts with the phosphonic acid functions, for example in the following manner:

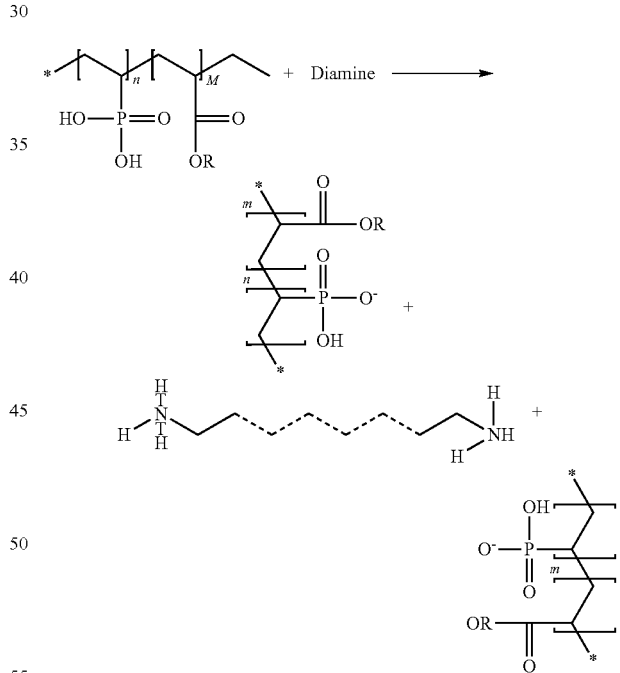

Other particular additional components may be used in the process according to the invention to contribute to improving the film-forming properties of the polymer according to the invention. Such additional components are in particular the salts of divalent or trivalent metal ions, clays and metal oxides described below.

The composition according to the invention may comprise salts of divalent or trivalent metal ions, chosen in particular from salts of ions derived from Al(III), Ca(II), Cu(II), Fe(II), Fe(III), Mg(II), Mn(II), Zn(II), and mixtures thereof. Ions derived from Ca(II), Mg(II) are preferred.

The salts of these metal ions are well known, with, for example, anions such as gluconate, chloride, sulfate, hydroxide, acetate and stearate. For example, use may be made of the following salts: calcium gluconate, calcium chloride, magnesium chloride, copper chloride, magnesium gluconate, iron sulfate, iron gluconate, aluminum sulfate, sodium stearate.

Said salts of divalent or trivalent metal ions may be present in the composition according to the invention in a content ranging from 0.1% to 20% by weight, preferably from 0.1% to 15% by weight, relative to the total weight of the composition.

Alternatively, the salt of divalent or trivalent metal ions may be applied sequentially in the process according to the invention.

The composition according to the invention may comprise a clay.

Clays are products that are already well known per se, which are described, for example, in the publication Minéralogie des argiles [Mineralogy of Clays], S. Caillère, S. Hénin, M. Rautureau, 2nd Edition 1982, Masson, the teaching of which is included herein by way of reference.

Among the clays, examples that may be mentioned include clays of the smectite family, such as laponite and montmorillonite, of the kaolinite family, such as kaolinite, dickite, nacrite, optionally modified clays of the halloysite, dombassite, antigorite, benthierine, pyrophyllite, montmorillonite, beidellite, vermiculite, talc, stevensite, hectorite, bentonite, saponite, chlorite, sepiolite and illite family.

The clay(s) present in the composition of the invention may be natural or synthetic. Natural clay is a sedimentary rock composed to a large extent of specific minerals, silicates generally of aluminum. Kaolin is thus a natural clay.

The clays may also be chemically modified by various compounds, such as acrylic acids, polysaccharides (for example carboxymethylcellulose) or organic cations.

Preferably, in the context of the present invention, use is made of clays that are cosmetically compatible with and acceptable for the hair, the skin and/or the scalp.

According to a particular embodiment of the present invention, the clay used is chosen from kaolinite, montmorillonites, saponites, laponites, bentonites, and in particular hectorites, and illites. Use is even more particularly made of mixtures of clays, and natural clays.

Natural clays that may be mentioned include green clays, in particular rich in illite; clays rich in montmorillonite, known as fuller's earth, or such as bentonites or else white clays rich in kaolinite. Bentonites that may be mentioned in particular include those sold under the names Bentone 38 VCG, Bentone Gel CAO V, Bentone 27 V, Bentone Gel MIO V and Bentone Gel ISD V by the company Elementis.

Montmorillonites and smectites are hydrated aluminum and/or magnesium silicates. Examples that may be mentioned include the montmorillonite sold under the name Gel White H by the company Rockwood Additives, and the purified smectite sold under the name Veegum Granules by the company Vanderbilt. Mention may also be made of the montmorillonite sold under the name Kunipia G4 by the company Kunimine and the sepiolite Pangel S9 sold by the company Tolsa.

Examples of kaolinites that may be mentioned include the kaolins sold under the name Coslin C 100 by the company BASF Personal Care Ingredients or Kaolin Supreme by the company Imerys.

Talcs are hydrated magnesium silicates usually comprising aluminum silicate. The crystal structure of talc is constituted of repeated layers of a sandwich of brucite between layers of silica. Examples that may be mentioned include micronized magnesium silicate of particle size 5 microns sold under the name Micro Ace P3 by the company Nippon Talc or the talcs sold under the names Rose Talc and Talc SG-2000 by the company Nippon Talc, J 68 BC by the company US Cosmetics (Miyoshi), Lyzenac 00 and Luzenac Pharma M by the company Luzenac, and Talc JA-46R by the company Asada Milling.

As saponite, which belongs to the montmorillonite family, mention may be made of synthetic saponite, in particular the product sold by the company Kunimine under the name Sumecton®.

An example of a synthetic laponite that may be mentioned is the laponite XLG sold by the company Rockwood.

The clay may be present in the composition according to the invention in an amount ranging from 0.1% to 50% by weight, in particular from 1% to 30% by weight and in particular from 1% to 20% by weight relative to the total weight of the composition.

The metal oxides may be chosen from titanium dioxide, iron oxides, zirconium oxides, zinc oxides, cerium oxides and chromium oxides. Iron oxides or titanium dioxide are preferably used.

The metal oxide may be in the composition according to the invention in an amount ranging from 0.1% to 50% by weight, in particular from 1% to 30% by weight and in particular from 1% to 20% by weight relative to the total weight of the composition.

The composition according to the invention is generally suitable for topical application to keratin materials, in particular to the skin, and thus generally comprises a physiologically acceptable medium, i.e. a medium that is compatible with the skin and/or its integuments. It is preferably a cosmetically acceptable medium, i.e. a medium which has a pleasant color, odor and feel and which does not cause any unacceptable discomfort (stinging, tautness or redness) liable to discourage the consumer from using this composition.

The composition according to the invention may be in any galenical form conventionally used for topical application and in particular in the form of dispersions of aqueous or oily gel or lotion type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. These compositions are prepared according to the usual methods.

According to one preferred embodiment of the invention, the composition is in the form of an O/W emulsion or an oily gel.

Advantageously, the composition according to the invention comprises an oil, in particular in a content that can range from 50% to 99% by weight.

The composition according to the invention may comprise a volatile oil.

For the purposes of the invention, the term "volatile oil" is intended to mean any oil that is capable of evaporating on contact with the skin, at ambient temperature and atmospheric pressure. The volatile oils of the invention are volatile cosmetic oils, which are liquid at ambient temperature, having a nonzero vapor pressure, at ambient temperature and atmospheric pressure, ranging in particular from 0.13 Pa to 40 000 Pa (0.001 to 300 mmHg) and preferably ranging from 1.3 Pa to 1300 Pa (0.01 to 10 mmHg).

These volatile oils may be hydrocarbon-based oils, in particular of animal or plant origin, silicone oils, or mixtures thereof. The term "hydrocarbon-based oil" is intended to mean an oil mainly containing hydrogen and carbon atoms and possibly oxygen, nitrogen, sulfur and/or phosphorus atoms.

The volatile hydrocarbon-based oils may be chosen from hydrocarbon-based oils having from 8 to 16 carbon atoms, and in particular branched $C_8$-$C_{16}$ alkanes such as $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade names Isopar® or Permethyl®.

Volatile oils that may also be used include volatile silicones, for instance volatile linear or cyclic silicone oils, in particular those with a viscosity≤5 centistokes ($5 \times 10^{-6}$ m²/s), and in particular containing from 2 to 10 silicon atoms and preferably from 2 to 7 silicon atoms, these silicones optionally comprising alkyl or alkoxy groups containing from 1 to 10 carbon atoms. As volatile silicone oils that may be used in the invention, mention may be made in particular of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The composition according to the invention may comprise a nonvolatile oil.

The term "nonvolatile oil" is intended to mean an oil that remains on the skin at ambient temperature and atmospheric pressure for at least several hours, and that in particular has a vapor pressure of less than 1.33 Pa (0.01 mmHg).

These nonvolatile oils may be hydrocarbon-based oils, in particular of animal or plant origin, silicone oils, or mixtures thereof. The term "hydrocarbon-based oil" is intended to mean an oil mainly containing hydrogen and carbon atoms and possibly oxygen, nitrogen, sulfur and/or phosphorus atoms.

The nonvolatile oils may be chosen in particular from nonvolatile hydrocarbon-based oils, which may be fluorinated, and/or nonvolatile silicone oils.

Nonvolatile hydrocarbon-based oils that may in particular be mentioned include:

hydrocarbon-based oils of animal origin, hydrocarbon-based oils of plant origin such as triglycerides constituted of fatty acid esters of glycerol, the fatty acids of which may have chain lengths varying from $C_4$ to $C_{24}$, these chains possibly being linear or branched, and saturated or unsaturated; these oils are in particular heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame oil, marrow oil, rapeseed oil, blackcurrant oil, evening primrose oil, millet oil, barley oil, *quinoa* oil, rye oil, safflower oil, candlenut oil, passionflower oil and musk rose oil; shea butter; or else caprylic/capric acid triglycerides, for instance those sold by the company Stéarineries Dubois or those sold under the names Miglyol 810®, 812® and 818® by the company Dynamit Nobel, synthetic ethers having from 10 to 40 carbon atoms;

linear or branched hydrocarbons of mineral or synthetic origin, such as petroleum jelly, polydecenes, hydrogenated polyisobutene such as Parleam®, squalane and liquid paraffins, and mixtures thereof, synthetic esters such as oils of formula $R_1COOR_2$ in which $R_1$ represents a linear or branched fatty acid residue containing from 1 to 40 carbon atoms and $R_2$ represents an, in particular branched, hydrocarbon-based chain containing from 1 to 40 carbon atoms, on condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at ambient temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol, higher fatty acids such as oleic acid, linoleic acid or linolenic acid, and mixtures thereof.

The nonvolatile silicone oils that may be used in the composition according to the invention may be nonvolatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, trimethylsiloxyphenyl dimethicones, phenyltrimethylsiloxydiphenylsiloxanes, diphenyl dimethicones, diphenylmethyldiphenyltrisiloxanes, and mixtures thereof.

The composition may be anhydrous. The term "anhydrous composition" is intended to mean a composition containing less than 2% by weight of water, or even less than 0.5% of water, and is in particular free of water. Where appropriate, such small amounts of water may in particular be introduced by ingredients of the composition that may contain residual amounts thereof.

The composition according to the invention may also contain one or more adjuvants commonly used in the cosmetics field, such as emulsifiers, preservatives, sequestering agents, fragrances, thickeners, oils, waxes, film-forming polymers, or colorants.

The composition according to the invention may also comprise a colorant such as pulverulent colorants, liposoluble dyes or water-soluble dyes. This colorant may be present in a content ranging from 0.01% to 30% by weight, relative to the total weight of the composition.

The pulverulent colorants may be chosen from pigments and nacres.

The pigments may be white or colored, mineral and/or organic, and coated or uncoated. Among the mineral pigments that may be mentioned are titanium dioxide, optionally surface-treated, zirconium, zinc or cerium oxides, and also iron or chromium oxides, manganese violet, ultramarine blue, chromium hydrate and ferric blue. Among the organic pigments that may be mentioned are carbon black, pigments of D&C type and lakes based on cochineal carmine or on barium, strontium, calcium or aluminum.

The nacres may be chosen from white nacreous pigments such as mica coated with titanium or with bismuth oxychloride, colored nacreous pigments such as titanium mica with iron oxides, titanium mica with in particular ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes are, for example, beetroot juice or methylene blue.

Needless to say, those skilled in the art will take care to select this or these optional additional compound(s), and/or the amount thereof, such that the anti-wrinkle properties of the composition according to the invention are not, or are not substantially, adversely affected by the envisaged addition.

According to a first embodiment of the process according to the invention, an extemporaneous mixture of a composition comprising the phosphonic polymer and of an amine compound as described previously or of a composition containing same and comprising a physiologically acceptable medium is applied to the skin. The extemporaneous mixture is advantageously prepared less than 5 minutes before it is applied to the skin, and preferably less than 3 minutes.

According to a second embodiment of the process according to the invention, the composition comprising the phosphonic polymer is first applied to the skin, and an amine compound as described previously or a composition containing same and comprising a physiologically acceptable medium is then applied. The application of the amine compound can be carried out after a time of between 5 minutes and one hour after having applied the phosphonic polymer.

According to a third embodiment of the process according to the invention, the amine compound, or a composition containing same and comprising a physiologically acceptable medium, is first applied to the skin, and the cosmetic composition comprising the phosphonic polymer is then applied. The application of the phosphonic polymer can be carried out after a time of between 5 minutes and one hour after having applied the amine compound.

The application of the composition according to the invention is performed according to the usual techniques, for example by application (in particular of creams, gels, sera or lotions) to the skin intended to be treated, in particular facial and/or neck skin, in particular the skin of the area around the eyes. In the context of this process, the composition may, for example, be a care composition.

The invention will now be described with reference to the following examples, which are given as non-limiting illustrations.

EXAMPLE 1

Isobornyl Acrylate/Vinylphosphonic Acid Copolymer (90/10 by Weight)

180 g of isobornyl acrylate, 20 g of vinylphosphonic acid and 200 g of an isododecane/ethanol (70/30 weight/weight) mixture were introduced into a reactor. The reaction medium was degassed under argon for 20 minutes. Then, 2 g of 2,5-dimethyl-2,5-di(2-ethylhexanoylperoxy)hexane initiator (Trigonox® T141 from Akzo Nobel) were added. The reaction medium was heated at reflux of the ethanol for 24 hours with stirring. After cooling to ambient temperature (25° C.), the reaction medium was diluted with 300 g of isododecane.

The product obtained was precipitated from ethanol, recovered and dried in an oven at 60° C. under vacuum.

180 g (90% yield) of a white powder were obtained after drying.

Molecular weight Mw=55 700.

The acid number is 21 mg/g.

EXAMPLE 2

Isobornyl Acrylate/Vinylphosphonic Acid Copolymer (80/20 by Weight)

The copolymer was prepared according to the procedure from example 1 using 160 g of isobornyl acrylate and 40 g of vinylphosphonic acid.

175 g (87.5% yield) of a white powder were obtained.

Molecular weight Mw=67 500.

The acid number is 31 mg/g.

EXAMPLE 3 (OUTSIDE THE INVENTION)

Isobornyl Acrylate/Acrylic Acid Copolymer (90/10 by Weight)

The copolymer was prepared according to the procedure from example 1 using 180 g of isobornyl acrylate and 20 g of acrylic acid.

140 g (70% yield) of a white powder were obtained.

The acid number is 18 mg/g.

EXAMPLE 4 (OUTSIDE THE INVENTION)

Isobornyl Acrylate/Acrylic Acid Copolymer (80/20 by Weight)

The copolymer was prepared according to the procedure from example 1 using 160 g of isobornyl acrylate and 40 g of acrylic acid.

150 g (75% yield) of a white powder were obtained.

The acid number is 110 mg/g.

EXAMPLE 5

Demonstration of the Tensioning Effect of the Polymers Used According to the Invention This test consists in comparing, in vitro, the tensioning capacity of the polymer to be evaluated, relative to a reference tensioning polymer: Hybridur® 875 polymer dispersion from Air Products (aqueous dispersion at 40% by weight of particles of an interpenetrated network of polyurethane and acrylic polymers). The polymer to be evaluated is deposited on a nitrile rubber strip cut from a glove sold under the reference Safeskin Nitrile Criticial No. 038846 by the company Dominique Dutscher SA, having a surface area of 3.5 $cm^2$, stretched taut beforehand on a support. A solution containing the polymer to be evaluated is therefore deposited on the elastomer strip, by depositing 1.8 mg (in solids) of polymer. 26 µl of an aqueous solution containing 7% AM of Hybridur® 875 polymer are thus placed on a nitrile rubber strip so as thus to obtain a reference tensioning strip, and 26 µl of a solution containing 7% AM of phosphonic polymer to be evaluated in an isododecane/ethanol mixture (70/30 weight/weight) are placed on another strip.

After drying for 24 hours at ambient temperature (25° C.), the curving (retraction) of the strip treated with the phosphonic polymer is observed in comparison with that obtained with the control (Hybridur® 875).

Also evaluated was the tensioning effect of the grafted polymer in the presence of 3-aminopropyltriethoxysilane (APTES) or of O,O'-Bis(2-aminopropyl) polypropylene glycol-block-polyethylene glycol-block-polypropylene glycol (Jeffamine® ED-600 from Huntsman) or of PDMS diamine (DMS-A15 from Gelest).

For the 3-aminopropyltriethoxysilane (APTES), the following mixtures were prepared before application to the nitrile strip (the phosphonic polymer being in solution in the isododecane/ethanol mixture):

| Ex | Degree of neutralization | Amount of polymer of example 1 (in g) | Number of moles of phosphonic acid | Amount of APTES (in mg) | Number of moles of amines |
|---|---|---|---|---|---|
| 1a | 25% | 0.7 | $2.625 \times 10^{-4}$ | 7.26 | $3.2813 \times 10^{-5}$ |
| 1b | 50% | 0.7 | $2.625 \times 10^{-4}$ | 14.52 | $6.5625 \times 10^{-5}$ |
| 1c | 100% | 0.7 | $2.625 \times 10^{-4}$ | 29.05 | $13.125 \times 10^{-5}$ |

| Ex | Degree of neutralization | Amount of polymer of example 2 (in g) | Number of moles of phosphonic acid | Amount of APTES (in mg) | Number of moles of amines |
|---|---|---|---|---|---|
| 2a | 25% | 0.7 | $4.125 \times 10^{-4}$ | 11.41 | $5.1563 \times 10^{-5}$ |
| 2b | 50% | 0.7 | $4.125 \times 10^{-4}$ | 22.82 | $10.3125 \times 10^{-5}$ |
| 2c | 100% | 0.7 | $4.125 \times 10^{-4}$ | 45.64 | $20.625 \times 10^{-5}$ |
| 2d | 200% | 0.7 | $4.125 \times 10^{-4}$ | 91.28 | $41.25 \times 10^{-5}$ |

For the O,O'-Bis(2-aminopropyl) polypropylene glycol-block-polyethylene glycol-block-polypropylene glycol (Jeffamine® ED-600 from Huntsman), the following mixtures were prepared before application to the nitrile strip (the phosphonic polymer being in solution in the isododecane/ethanol mixture):

| ex | Degree of neutralization | Amount of polymer of example 1 (in g) | Number of moles of phosphonic acid | Amount of Jeffamine ® ED-600 (in mg) | Number of moles of amines |
|---|---|---|---|---|---|
| 1e | 25% | 0.7 | $2.625 \cdot 10^{-4}$ | 10 | $3.2813 \times 10^{-5}$ |
| 1f | 100% | 0.7 | $2.625 \times 10^{-4}$ | 40 | $13.125 \times 10^{-5}$ |

For the PDMS diamine (DMS-A15 from Gelest), the following mixtures were prepared before application to the nitrile strip (the phosphonic polymer being in solution in the isododecane/ethanol mixture):

| ex | Degree of neutralization | Amount of polymer of example 1 (in g) | Number of moles of phosphonic acid | Amount of PDMS diamine (in mg) | Number of moles of amines |
|---|---|---|---|---|---|
| 1g | 25% | 0.7 | $2.625 \cdot 10^{-4}$ | 41 | $3.2813 \times 10^{-5}$ |
| 1h | 50% | 0.7 | $2.625 \times 10^{-4}$ | 82 | $6.5625 \times 10^{-5}$ |
| 1i | 100% | 0.7 | $2.625 \times 10^{-4}$ | 164 | $13.125 \times 10^{-5}$ |

The mixtures prepared were deposited (26 µl) on the nitrile rubber strips.

The tensioning effect obtained was measured according to the protocol previously described.

The water resistance of the tensioning effect was then evaluated by immersing the rubber strips treated with the polymer to be evaluated in water at ambient temperature (25° C.) for 10 minutes.

The following results were obtained:

| Polymer tested | Tensioning effect | Tensioning effect after immersion in water |
|---|---|---|
| Hybridure 875 reference | correct | correct |
| Example 1 | same as reference | same as reference |
| Example 1a | greater than the reference | greater than the reference |
| Example 1b | same as reference | same as reference |
| Example 1c | same as reference | same as reference |
| Example 2 | same as reference | same as reference |
| Example 2a | same as reference | greater than the reference |
| Example 2b | same as reference | greater than the reference |
| Example 2c | greater than the reference | greater than the reference |
| Example 2d | greater than the reference | greater than the reference |
| Example 1e | less than the reference but tensioning effect observed | less than the reference but tensioning effect observed |
| Example 1f | less than the reference but tensioning effect observed | less than the reference but tensioning effect observed |
| Example 1g | less than the reference but tensioning effect observed | same as reference |
| Example 1h | same as reference | same as reference |
| Example 1i | Same as reference | same as reference |

The results obtained show that the phosphonic polymers of examples 1 and 2 alone or mixed with the amine compounds have a good tensioning effect, even after immersion in water: the tensioning effect is persistent with respect to water.

EXAMPLE 6 (COMPARATIVE)

The quality of the films obtained, with the polymers from examples 1 and 2 according to the invention and also with the polymers from examples 3 and 4 outside the invention, was evaluated.

The polymers were placed in solution at 7% AM in a (70/30) mixture of isododecane/ethanol. 26 µl of the polymer solution were applied to a nitrile rubber strip (as described in the previous example) and the appearance of the film obtained was observed after drying in the open air for 24 hours at ambient temperature.

Polymers 1 and 2 according to the invention form homogeneous transparent films, while polymers 3 and 4 outside the invention form films which are white (non-transparent) and non-homogeneous (crumbly film).

EXAMPLE 7

An anti-wrinkle gel having the following composition is prepared:

| | |
|---|---|
| polymer of example 1 | 7 g |
| disteardimonium hectorite/propylene carbonate in isododecane (bentone gel ® ISDV from Elementis) | 3 g |

-continued

| | |
|---|---|
| Preservatives | qs |
| Isododecane/ethanol (80/20 w/w) | qs |
| | 100 g |

A similar composition was also prepared using the polymer of example 2.

The composition obtained, applied to the face, makes it possible to effectively smooth out wrinkles.

EXAMPLE 8

An anti-wrinkle gel having the following composition is prepared:

| | |
|---|---|
| polymer of example 1 | 7 g |
| disteardimonium hectorite/propylene carbonate in isododecane (bentone gel ® ISDV from Elementis) | 3 g |
| Preservatives | qs |
| Isododecane/ethanol (80/20 w/w) | qs |
| | 100 g |

Just before application to the skin, 145.2 mg of 3-aminopropyltriethoxysilane (APTES) are added to the gel.

The composition obtained, as a mixture with APTES, applied to the face, makes it possible to effectively smooth out the wrinkles.

EXAMPLE 9

An anti-wrinkle gel having the following composition is prepared:

| | |
|---|---|
| polymer of example 2 | 7 g |
| disteardimonium hectorite/propylene carbonate in isododecane (bentone gel ® ISDV from Elementis) | 3 g |
| Preservatives | qs |
| Isododecane/ethanol (80/20 w/w) | qs |
| | 100 g |

Just before application to the skin, 228.2 mg of 3-aminopropyltriethoxysilane (APTES) are added to the gel.

The composition obtained, as a mixture with APTES, applied to the face, makes it possible to effectively smooth out the wrinkles.

EXAMPLE 10

An anti-wrinkle gel having the following composition is prepared:

| | |
|---|---|
| polymer of example 1 | 7 g |
| disteardimonium hectorite/propylene carbonate in isododecane (bentone gel ® ISDV from Elementis) | 3 g |
| Preservatives | qs |
| Isododecane/ethanol (80/20 w/w) | qs |
| | 100 g |

Just before application to the skin, 820 mg of PDMS diamine (DMS-A15 from Gelest) are added to the gel.

The composition obtained, as a mixture with PDMS diamine, applied to the face makes it possible to effectively smooth out the wrinkles.

EXAMPLE 11

An anti-wrinkle gel having the following composition is prepared:

| | |
|---|---|
| polymer of example 2 | 7 g |
| disteardimonium hectorite/propylene carbonate in isododecane (bentone gel ® ISDV from Elementis) | 3 g |
| Preservatives | qs |
| Isododecane/ethanol (80/20 w/w) | qs |
| | 100 g |

The composition is applied to the wrinkled skin of the face. It is left to dry for 1 hour.

The following solution is then applied to the area of the skin treated:

| | |
|---|---|
| 3-aminopropyltriethoxysilane (APTES) | 145.2 mg |
| Isododecane/ethanol (80/20 w/w) | qs |
| | 100 g | and it is left to dry for 1 hour.

The sequential application of the 2 compositions to the face makes it possible to effectively smooth out the wrinkles.

EXAMPLES 12 TO 14

The 3 compositions described below were prepared.

Each composition was applied onto a skin equivalent support made of elastomer by producing a deposit with a wet thickness of 100 μm, which was left to dry at ambient temperature (25° C.) for 24 hours.

The state of the film obtained was then observed.

The resistance of the film obtained was evaluated by separately applying 0.5 ml of olive oil and 0.5 ml of sebum; after 5 minutes of contact, the surface of the film was rubbed with cotton wool and the state of the film was then observed.

The tackiness of the film and its capacity for transferring or not transferring on touching the film with a finger were also evaluated.

The following results were obtained:

| | Example 12 | Example 13 | Example 14 |
|---|---|---|---|
| Polymer of example 1 | 25 g | 25 g | 25 g |
| PDMS diamine (DMS-A15 from Gelest) | 0 | 3.75 g | 7.5 g |
| Isododecane:ethanol (70/30 w/w) | qs 100 g | qs 100 g | qs 100 g |
| Appearance of the film | Homogeneous film | Homogeneous film | Homogeneous film |
| Olive oil resistance | + | +++ | +++ |
| Sebum resistance | + | +++ | +++ |
| Non-tacky | +++ | +++ | +++ |
| Transfer-resistant | +++ | +++ | +++ |

The results obtained show that polymer 1 alone or in the presence of PDMS diamine forms a homogeneous film which is non-tacky and does not transfer to the finger. The resistance of the film on contact with olive oil and sebum is much improved in the presence of PDMS diamine.

EXAMPLES 15 TO 18

The 4 compositions described below were prepared.
The film-forming properties were then evaluated according to the protocols described in examples 12 to 14.
The following results were obtained:

|  | Ex 15 | Ex 16 | Ex 17 | Ex 18 |
|---|---|---|---|---|
| Polymer of example 1 | 25 g | 25 g | 25 g | 25 g |
| PDMS diamine (DMS-A15 from Gelest) | 0 | 3.75 |  | 3.75 g |
| pigmentary paste containing 40% by weight of iron oxide in isododecane | — | — | 5 g | 5 g |
| 2-Octyldodecanol | 20 g | 20 | 20 | 20 g |
| Isododecane | qs 100 g | qs 100 g | qs 100 g | qs 100 g |
| Appearance of the film | Homogeneous film | Homogeneous film | Homogeneous film | Homogeneous film |
| Olive oil resistance | + | +++ | +++ | +++ |
| Sebum resistance | + | +++ | +++ | +++ |
| Non-tacky | + | +++ | + | +++ |
| Transfer-resistant | +++ | +++ | +++ | +++ |

The results obtained show that polymer 1 alone (ex 15) or in the presence of PDMS diamine (ex 16) and formulated with 2-octyldodecanol (nonvolatile oil) forms a homogeneous film which is non-tacky and does not transfer to the finger. The resistance of the film on contact with olive oil and sebum is much improved in the presence of PDMS diamine.

When iron oxide is added, an improvement in the resistance to olive oil and to sebum is noted (examples 17 and 18 in comparison with example 15).

EXAMPLE 19

The foundation composition described below was prepared.
The film-forming properties were then evaluated according to the protocols described in examples 12 to 14.
The following results were obtained:

|  | Example 19 |
|---|---|
| Polymer of example 1 | 25 g |
| pigmentary paste containing 40% by weight of iron oxide in isododecane | 5 g |
| Disteardimonium Hectorite (Bentone Gel ISD V from Elementis) | 10 g |
| 2-Octyldodecanol | 20 g |
| Isododecane: | qs 100 g |
| Appearance of the film | Homogeneous film |
| Olive oil resistance | +++ |
| Sebum resistance | +++ |
| Non-tacky | +++ |
| Transfer-resistant | +++ |

The results obtained show that the foundation composition forms a homogeneous film which is non-tacky and does not transfer to the finger. The film obtained also exhibits good resistance on contact with olive oil and sebum, much improved in the presence of the bentone compared with the polymer alone (example 15).

The foundation applied to the skin of the face thus makes it possible to obtain a non-tacky, transfer-resistant and sebum-resistant makeup which therefore exhibits a good wear property.

The invention claimed is:

1. A copolymer resulting from the polymerization of:
   (i) 70% to 95% by weight, of the total weight of the monomers, of isobornyl (meth)acrylate;
   (ii) 1% to 30% by weight of vinylphosphonic acid monomer of formula (I):

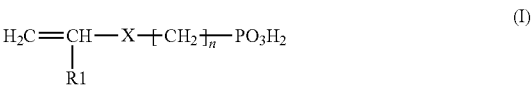

in which:
   R1 denotes H or —CH$_3$;
   X denotes a covalent bond and n denotes an integer ranging from 0 to 14;
   or X denotes a —COO— group and n denotes an integer ranging from 2 to 6;
   (iii) 0 to 20% by weight of an additional monomer.

2. The copolymer as claimed in claim 1, wherein, for monomer (I):
   X denotes a covalent bond and n is an integer ranging from 0 to 6 or X denotes a —COO— group and n is an integer ranging from 2 to 4.

3. The copolymer as claimed in claim 1, wherein, for monomer (I), R1=H and X denotes a covalent bond and n is an integer ranging from 0 to 4.

4. The copolymer as claimed in claim 1, wherein monomer (I) is chosen from:
   vinylphosphonic acid;
   3-butenylphosphonic acid;
   4-pentenylphosphonic acid;
   10-undecenylphosphonic acid;
   11-dodecenylphosphonic acid;
   2-phosphonoethyl ester of 2-methyl-2-propenoic acid;
   2-phosphonoethyl ester of 2-propenoic acid.

5. The copolymer as claimed in claim 1, wherein the additional monomer is a monomer of formula (II):

in which:
   $R_1$ denotes a hydrogen atom or a methyl radical;
   X denotes O or NH or NR$_3$;
   $R_2$ denotes a linear $C_1$-$C_{22}$ or branched $C_3$-$C_{10}$ or cyclic $C_5$-$C_7$ alkyl radical, or a linear $C_3$-$C_{20}$ or branched $C_6$-$C_{20}$ or cyclic $C_5$-$C_7$ unsaturated hydrocarbon-based radical, or an —(Si(CH$_3$)$_2$O)$_b$—CH$_3$ radical, with b ranging from 5 to 70, it being understood that X=O when $R_2$ is a radical of formula —(Si(CH$_3$)$_2$O)$_b$—CH$_3$;

$R_3$ denotes a linear $C_1$-$C_{12}$ or branched $C_3$-$C_{12}$ alkyl radical.

6. The copolymer as claimed in claim 1, which results from the polymerization of:
   70% to 95% by weight, of the total weight of the monomers, of isobornyl (meth)acrylate;
   5% to 30% by weight of vinylphosphonic acid.

7. The copolymer as claimed in claim 1, which is chosen from 80/20 or 90/10 (weight/weight) isobornyl acrylate/vinylphosphonic acid copolymers.

8. The copolymer as claimed in claim 1, which is a random copolymer.

9. A composition comprising, in a physiologically acceptable medium, a copolymer as claimed in claim 1.

10. A kit comprising a first composition as claimed in claim 9 and a second composition comprising an additional compound chosen from:
    (i) an amine compound chosen from amine compounds bearing several primary amine and/or secondary amine groups and aminosilanes,
    (ii) salts of divalent or trivalent metal ions,
    (iii) clays, and
    (iv) metal oxides,
       or of a composition containing said additional component and comprising a physiologically acceptable medium, the first and second compositions each being packaged in a separate packaging assembly.

11. A composition obtained by mixing a composition as claimed in claim 9 and an additional component chosen from:
    (i) an amine compound chosen from amine compounds bearing primary amine and/or secondary amine groups and aminosilanes,
    (ii) salts of divalent or trivalent metal ions,
    (iii) clays, and
    (iv) metal oxides,
       or a composition containing said additional component and comprising a physiologically acceptable medium.

12. The composition as claimed in in claim 9, wherein the copolymer is present in a content ranging from 0.1% to 10% by weight, relative to the total weight of the composition.

13. A process for caring for or making up keratin materials, comprising the topical application to the keratin materials of a composition as claimed in claim 9.

14. The process as claimed in claim 13, wherein the topical application, to keratin materials, of an extemporaneous mixture of (A) a composition comprising, in a physiologically acceptable medium, a copolymer resulting from the polymerization of:
    (i) 70% to 95% by weight, of the total weight of the monomers, of isobornyl (meth)acrylate;
    (ii) 1% to 30% by weight of vinylphosphonic acid monomer of formula (I):

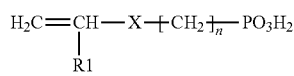

(I)

in which:
   R1 denotes H or —CH$_3$;
   X denotes a covalent bond and n denotes an integer ranging from 0 to 14;

or X denotes a —COO— group and n denotes an integer ranging from 2 to 6;
    (iii) 0 to 20% by weight of an additional monomer; and
(B) of an additional component chosen from:
    (i) an amine compound chosen from amine compounds bearing primary amine and/or secondary amine groups and aminosilanes,
    (ii) salts of divalent or trivalent metal ions,
    (iii) clays, and
    (iv) metal oxides,
       or of a composition containing said additional component and comprising a physiologically acceptable medium, is carried out.

15. The process as claimed in claim 14, wherein the amine compound has 2 to 20 carbon atoms.

16. The process as claimed in claim 14, wherein the amine compound is chosen from N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethy)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine, lysine, cystamine, xylenediamine, tris(2-aminoethyl)amine and spermidine; and the aminosilanes of formula (III):

(III)

in which:
   R'$_1$ is a linear or branched, saturated or unsaturated, cyclic or acyclic $C_1$-$C_6$ hydrocarbon-based chain substituted with a group chosen from the following groups:
      amine NH$_2$ or NHR with R=$C_1$-$C_4$ alkyl,
      an aryl or aryloxy group substituted with an amino group or with a $C_1$-$C_4$ aminoalkyl group,
      R'$_1$ possibly being interrupted in its chain with a heteroatom O, S, NH) or a carbonyl group (CO), R'$_1$ being linked to the silicon atom directly via a carbon atom,
   R'$_2$ and R'$_3$, which may be identical or different, represent a linear or branched alkyl group comprising from 1 to 6 carbon atoms,
   z denotes an integer ranging from 1 to 3, and
   x denotes an integer ranging from 0 to 2,
with z+x=3.

17. The process as claimed in claim 14, wherein the amine compound is chosen from amine-based polymers.

18. The process as claimed in in claim 17, wherein the amine compound is an amine-based polymer chosen from poly(($C_2$-$C_5$)alkyleneimines); amino polyvinyl alcohol, acrylamidopropylamine-based copolymers; chitosans; polydimethylsiloxanes comprising primary amine groups at the chain end or on side chains; polytetrahydrofuran α,ω-diamines and polybutadiene α,ω-diamines; polyamidoamine dendrimers bearing amine end functions; poly(meth)acrylates or poly(meth)acrylamides bearing primary or secondary amine side functions.

19. The process as claimed in claim 14, wherein the amine compound is used according to an amine compound/phosphonic acid mole ratio ranging from 0.01 to 10.

20. The process as claimed in claim 14, wherein the additional component is a clay chosen from clays of the smectite family, of the kaolinite family, optionally modified clays of the halloysite, dombassite, antigorite, benthierine, pyrophyllite, montmorillonite, beidellite, vermiculite, talc, stevensite, hectorite, bentonite, saponite, chlorite, sepiolite and illite family.

21. The process as claimed in claim 14, wherein the additional component is a salt of divalent or trivalent metal ions chosen from salts of ions derived from Al(III), Ca(II), Cu(II), Fe(II), Fe(III), Mg(II), Mn(II), Zn(II) and mixtures thereof.

22. The process as claimed in claim 14, wherein the additional component is a metal oxide chosen from titanium dioxide, iron oxides, zirconium oxides, zinc oxides, cerium oxides and chromium oxides.

23. The process as claimed in claim 14, wherein an extemporaneous mixture prepared less than 5 minutes before application to keratin materials of (A) a composition comprising, in a physiologically acceptable medium, a copolymer resulting from the polymerization of:
(i) 70% to 95% by weight, of the total weight of the monomers, of isobornyl (meth)acrylate;
(ii) 1% to 30% by weight of vinylphosphonic acid monomer of formula (I):

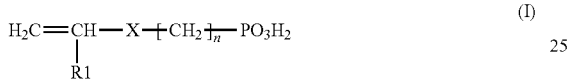

in which:
R1 denotes H or —CH$_3$;
X denotes a covalent bond and n denotes an integer ranging from 0 to 14;
or X denotes a —COO— group and n denotes an integer ranging from 2 to 6;
(iii) 0 to 20% by weight of an additional monomer; and
(B) of said additional component, or of a composition containing said additional component and comprising a physiologically acceptable medium, is applied to keratin materials.

24. The process as claimed in claim 13, which comprises the sequential application, to keratin materials, of (A) a composition comprising, in a physiologically acceptable medium, a copolymer resulting from the polymerization of:
(i) 70% to 95% by weight, of the total weight of the monomers, of isobornyl (meth)acrylate;
(ii) 1% to 30% by weight of vinylphosphonic acid monomer of formula (I):

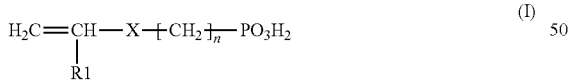

in which:
R1 denotes H or —CH$_3$;
X denotes a covalent bond and n denotes an integer ranging from 0 to 14;
or X denotes a —COO— group and n denotes an integer ranging from 2 to 6;
(iii) 0 to 20% by weight of an additional monomer; and
(B) of an additional component chosen from:
(i) an amine compound chosen from amine compounds comprising several primary amine and/or secondary amine groups and aminosilanes,
(ii) salts of divalent or trivalent metal ions,
(iii) clays, and
(iv) metal oxides, or of a composition containing said additional component and comprising a physiologically acceptable medium, is carried out.

25. The process as claimed in claim 24, wherein a composition comprising, in a physiologically acceptable medium, a copolymer resulting from the polymerization of:
(i) 70% to 95% by weight, of the total weight of the monomers, of isobornyl (meth)acrylate;
(ii) 1% to 30% by weight of vinylphosphonic acid monomer of formula (I):

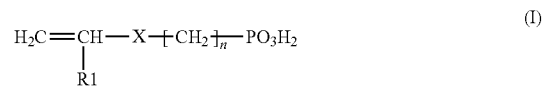

in which:
R1 denotes H or —CH$_3$;
X denotes a covalent bond and n denotes an integer ranging from 0 to 14;
or X denotes a —COO— group and n denotes an integer ranging from 2 to 6;
(iii) 0 to 20% by weight of an additional monomer is first applied to keratin materials, then said additional component or a composition containing said additional component and comprising a physiologically acceptable medium is applied.

26. The process as claimed in in claim 24, wherein said additional component, or a composition containing said additional component and comprising a physiologically acceptable medium, is first applied to keratin materials, then a composition comprising, in a physiologically acceptable medium, a copolymer resulting from the polymerization of:
(i) 70% to 95% by weight, of the total weight of the monomers, of isobornyl (meth)acrylate;
(ii) 1% to 30% by weight of vinylphosphonic acid monomer of formula (I):

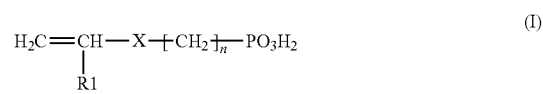

in which:
R1 denotes H or —CH$_3$;
X denotes a covalent bond and n denotes an integer ranging from 0 to 14;
or X denotes a —COO— group and n denotes an integer ranging from 2 to 6;
(iii) 0 to 20% by weight of an additional monomer is applied.

27. The process as claimed in claim 13 the composition comprises an oil.

28. The process as claimed in claim 13, wherein the keratin materials is the skin.

29. The process as claimed in claim 13, which comprises attenuating wrinkles.

30. A cosmetic process for treating skin which comprises applying to the skin a phosphonic polymer as defined in claim 1 and optionally as a mixture with an additional compound chosen from:
(i) an amine compound chosen from amine compounds bearing primary amine and/or secondary amine groups and aminosilanes, (ii) salts of divalent or trivalent metal ions,
(iii) clays, and
(iv) metal oxides,
or of a composition containing said additional component; thereby causing tensioning of the skin.

* * * * *